(12) United States Patent
Bawden et al.

(10) Patent No.: US 8,857,280 B2
(45) Date of Patent: Oct. 14, 2014

(54) SCREENED INLINE FLOW-THROUGH (SIFT) SEDIMENT TRAP APPARATUS

(75) Inventors: Jeremiah Bawden, Portland, OR (US); Randy Christopher Belson, Portland, OR (US); Matthew Joseph Sullivan, Portland, OR (US)

(73) Assignee: City of Portland, Portland, OR (US)

( * ) Notice: Subject to any disclaimer, the term of this patent is extended or adjusted under 35 U.S.C. 154(b) by 324 days.

(21) Appl. No.: 13/217,504

(22) Filed: Aug. 25, 2011

(65) Prior Publication Data
US 2013/0048576 A1    Feb. 28, 2013

(51) Int. Cl.
*G01N 1/10* (2006.01)
*F16L 55/24* (2006.01)
*E03F 5/14* (2006.01)

(52) U.S. Cl.
CPC .......... *E03F 5/14* (2013.01); *G01N 2001/1025* (2013.01); *F16L 55/24* (2013.01); *G01N 2001/1093* (2013.01); *G01N 2001/1012* (2013.01)
USPC ...................................... 73/863.23

(58) Field of Classification Search
None
See application file for complete search history.

(56) References Cited

U.S. PATENT DOCUMENTS

| | | | |
|---|---|---|---|
| 3,085,425 A * | 4/1963 | Roman | 73/61.71 |
| 3,751,734 A * | 8/1973 | Lumadue | 4/679 |
| 4,271,704 A | 6/1981 | Peter | |
| 4,303,533 A | 12/1981 | Freemont | |
| 4,590,810 A | 5/1986 | Hunkin et al. | |
| 4,762,009 A * | 8/1988 | Scrudto | 73/863.52 |
| 5,339,700 A | 8/1994 | Wright et al. | |
| 5,397,464 A | 3/1995 | Hannon | |
| 6,006,612 A | 12/1999 | Nurse, Jr. et al. | |
| 2004/0187611 A1 | 9/2004 | Leoncavallo | |

* cited by examiner

*Primary Examiner* — Robert R Raevis
(74) *Attorney, Agent, or Firm* — Kolisch Hartwell, P.C.

(57) ABSTRACT

An improved sediment trap is adapted for inline placement in a pipe. The sediment trap includes a housing body defining two chambers with an intermediate screen member disposed therebetween. The first chamber includes at least one sidewall coupled to a partial front wall wherein the partial front wall, which is disposed at an end opposite from the intermediate screen member. The second chamber includes at least one sidewall and a rear mesh screen. When placed in-line, the effluent stream deposits solids of a first size in the first chamber and deposits solids of a second size in the second chamber.

10 Claims, 8 Drawing Sheets

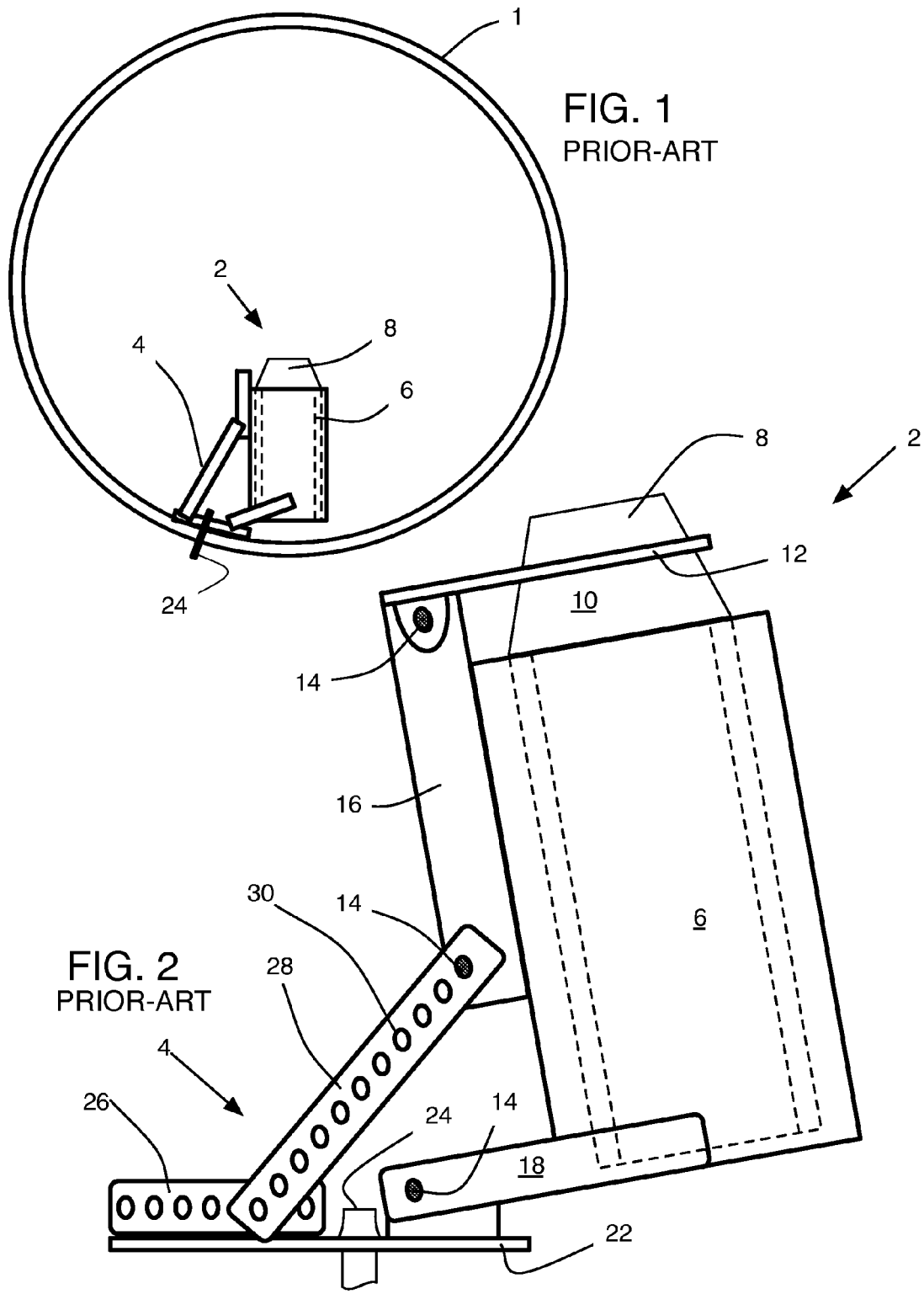

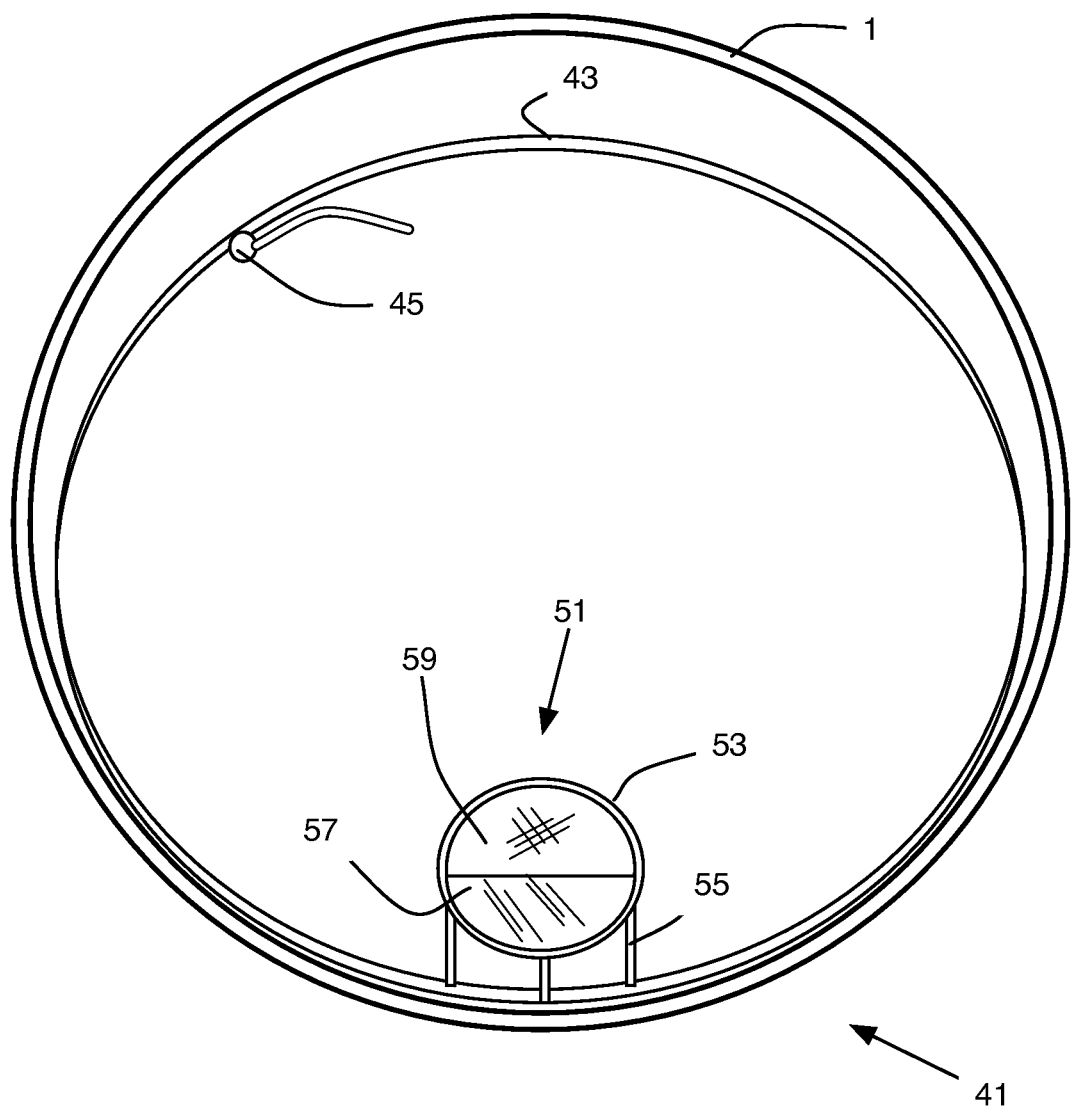

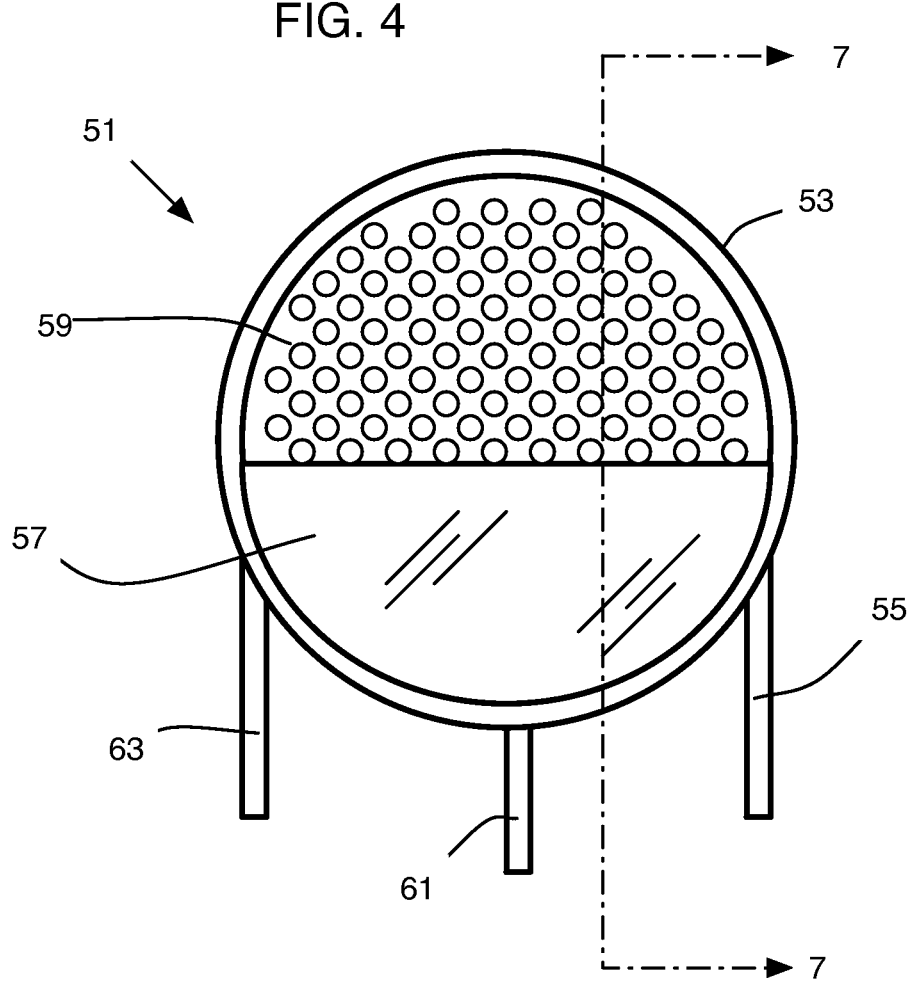

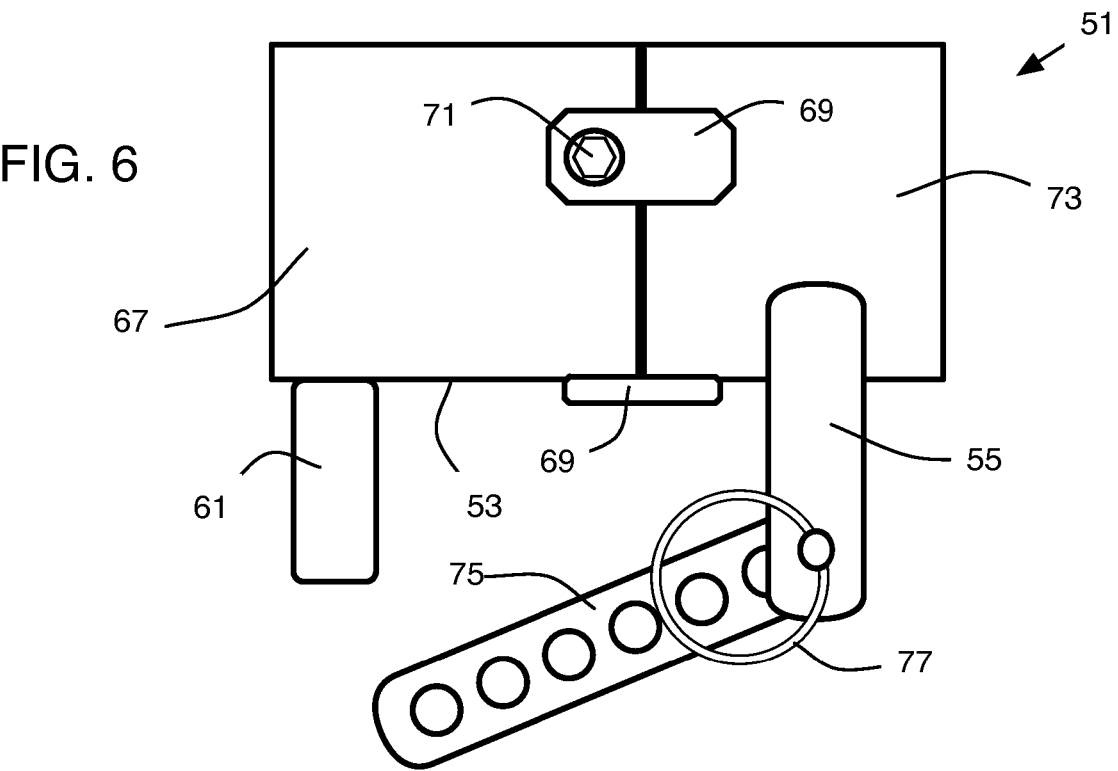
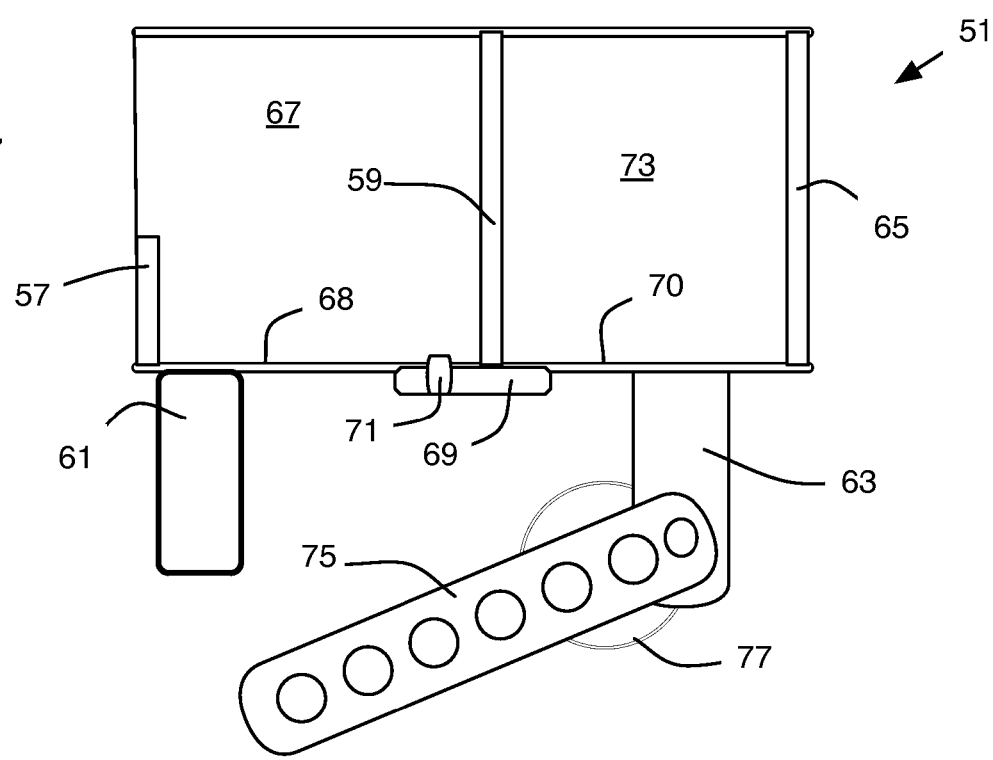

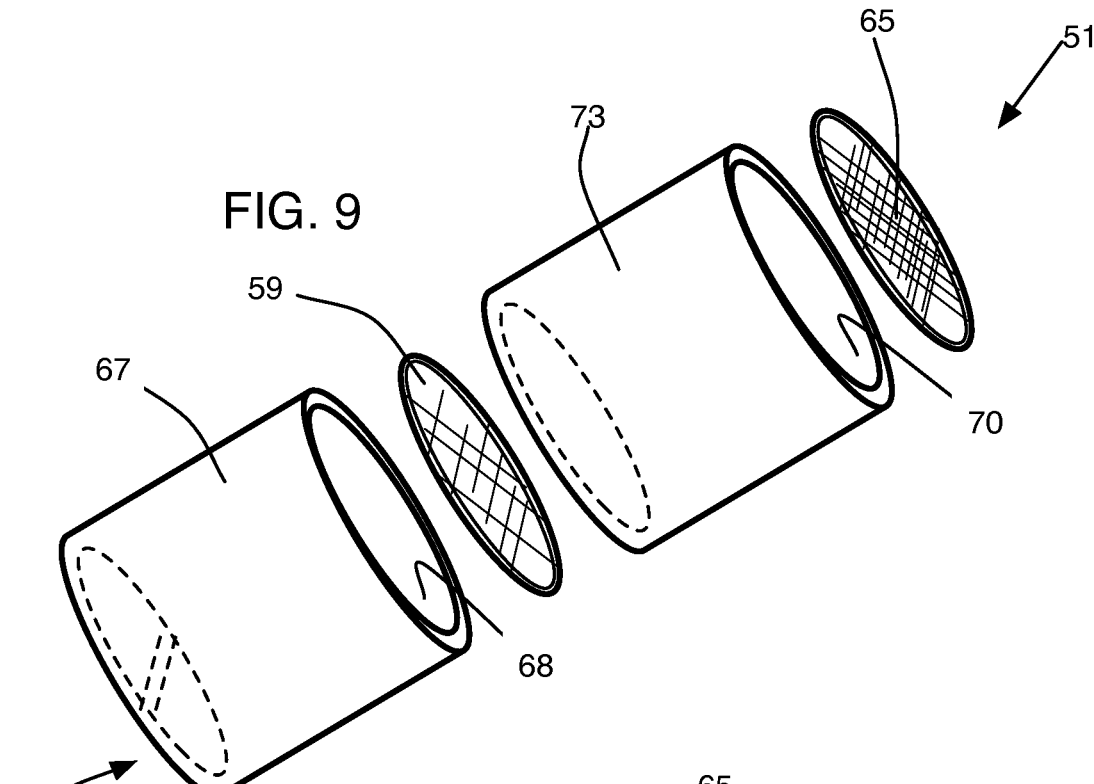
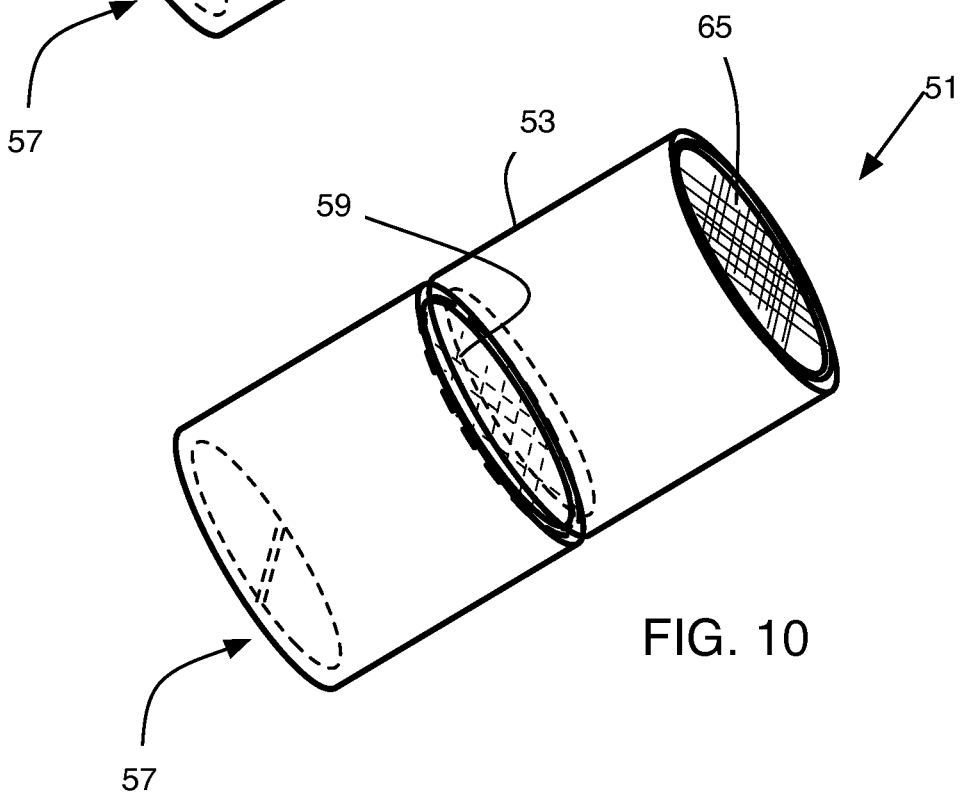

SCREENED INLINE FLOW-THROUGH (SIFT) SEDIMENT TRAP APPARATUS

BACKGROUND

The present invention relates to collection devices that arrange inside pipelines and similar fluid conveyance systems to trap samples and, more specifically, devices placed in stormwater pipelines to collect suspended sediment samples.

Inline sediment traps are one of many sampling tools utilized by municipalities, environmental agencies, and private parties to characterize piped pathways to receiving waters and to support ongoing contaminant investigations. A known sediment trap apparatus consists of a stainless steel bracket that bolts to the pipeline wall and the bracket supports a cylindrical housing fixture. The cylindrical housing fixture supports a 1-liter (L) high-density polyethylene (HDPE) sample bottle. The sample bottle is retained in the fixture by a securing band placed around the neck of the sample bottle, and the sample-bottle's open top arranges generally perpendicular to the flow of the effluent stream (see FIG. 1).

This known type of inline sediment trap is commonly deployed; yet, these trap deployments have captured insufficient volumes of stormwater solids to meet all analytical objectives, such as in a City of Portland (Oregon, USA) study where installed sediment traps were placed in a variety of locations within the stormwater conveyance system during the 2007 and 2008 wet seasons.

Despite the variety of known sediment traps in the art, there are several shortcomings that need to be overcome to provide a more efficient sample collection method and to provide more flexibility when installing devices in various diameter pipelines. These, and other, shortcomings and limitations of known collection devices were exposed during field use in Portland, Oreg., during the wet season in 2007, 2008, and 2009 when sediment samples were collected using various prior-art sediment trap designs. From this collection effort various observations of limitations in the known art were made and such limitations included that the bottle-type sediment traps required significant labor hours to install, and significant labor hours to separate the sediment from the fluid in the lab at the end of a deployment period before solids analysis. Other limitations include a large profile, and the resulting inability to be easily installed and removed or to capture adequate stormwater solids in small-pipe diameters (i.e., in pipe diameters less than 30 inches).

Other known collection devices include a system taught by Leoncavallo et al. in U.S. Pat. App. No. US 2004/0187611 published on 30 Sep. 2004. Leoncavallo describes a liquid sample collection system including a container having an interior reservoir for receiving a sample and a valve assembly that couples to the container. The valve assembly includes a separator configured to inhibit particulate material from entering the valve-housing inlet and reservoir.

Another known collection device, taught by Peters on 9 Jun. 1981 in U.S. Pat. No. 4,271,704, consists of a fluid sampling device including a body having a chamber and a control valve disposed in a control passageway and a sample valve disposed in a sampling passageway. Another device, in U.S. Pat. No. 4,303,533 to Fremont on 1 Dec. 1981, includes passing the stream through at least two contiguous layers of an open-celled compressible hydrophobic polymeric material. Yet another device, by Hannon on 14 Mar. 1995, U.S. Pat. No. 5,397,464, consists of a trough-type strainer box or basket with a mounting flange on its upper edge for supporting the basket in a floor sink to capture particulates. And another device, by Nurse, Jr. et al. on 28 Dec. 1999, U.S. Pat. No. 6,006,612, consists of a test assembly for sampling effluent waste water. The assembly includes two parallel testing lines, one of which includes a filter, the second of which contains—in one version—a second type of filter or—in a second version—no filter.

Further afield from a desired collection device, other teachings in the art include U.S. Pat. No. 4,590,810 issued on 27 May 1986 to Hunkin et al., which describes a device for collecting samples of water from wells. The device includes valves at both ends. And, U.S. Pat. No. 5,339,700 issued to Wright et al. on 23 Aug. 1994 describes a sample collector for drawing samples of a liquid by means of a pump near an inlet port.

Thus, there remains a need for a better sediment collection device that fits in various diameter pipelines including diameters less than 30-inches, requires less time to install and remove, improves the collection of sediment, and reduces laboratory processing time.

SUMMARY OF THE INVENTION

Inline sediment traps are one of many sampling tools utilized by the City of Portland for investigating contaminant sources to the City stormwater conveyance system. The Bureau of Environmental Services Field Operations section (FO) was tasked to install sediment traps in a variety of locations within the stormwater conveyance system during winter wet seasons in support of these efforts.

The standard sediment trap design, which had been used for all site deployments prior to 2009, consists of a stainless steel bracket and cylinder that houses a 1-L, high-density polyethylene (HDPE) sample bottle. The trap itself is mounted in-situ to the bottom of a pipe via stainless steel concrete anchor bolts.

The majority of the inline sediment trap deployments to date have captured insufficient volumes of stormwater solids to meet all analytical objectives, and as such, an additional pilot study was conducted to evaluate how variables such as trap design, bottle shape, and bottle aperture affect captured stormwater solids volumes.

Alternate sediment trap designs and different bottle types tested during this study included: a standard 1-L HDPE round, narrow-mouth bottle (bottle type used for current sediment trap design); a standard 1-L HDPE round, wide-mouth bottle; a rectangular 1-L HDPE, wide-mouth bottle; a square 1-L HDPE, wide-mouth bottle; and an embodiment of the present invention—a stainless steel Screened Inline Flow-through (SIFT) sediment trap prototype. This prototype consists of two bracketed, stainless steel cylinders. The upstream cylinder has an attached 1.5-inch high stainless steel weir, and a stamped, 18-gauge stainless steel mesh back plate (~1270 µm—medium sands). The downstream secondary cylinder has a stainless steel, fine mesh screen (~228 µm—fine sands/silts), backed by a stamped, 18-gauge stainless steel mesh back plate.

Throughout the duration of this study, field crews observed variable stormwater solids capture rates per trap at all five sites. Initially, this was theorized to be a correlation between bottle aperture and/or bottle shape. It was also theorized that the sediment trap alignments may have altered the flow regimes at each of the sites. Additionally, based on both field observations and an analysis of the solids accumulation data, there appeared to be a spatial component to these solids capture rates.

This variability in which bottle types and/or aperture captured the most solids during this study does not allow for a conclusive decision to be made at this time as to which conventional bottle will best meet the analytical objectives for this project.

Conversely, the evaluation of the SIFT prototype embodiment of the present invention showed promising solids capture rates during this study. The total captured solids submitted for analysis from this prototype at the conclusion of this study was 41.5-grams (g). In contrast, two standard sediment traps, both equipped with standard narrow-mouth bottles, were installed and resulted in a total captured solids submitted for analysis of 10.8-g. Approximately four times more stormwater solids were captured via the SIFT prototype compared to the solids captured by the two standard inline sediment traps.

One of these advantages is that the SIFT prototype appears to capture a measurable portion of the solids fraction from discrete storm events, resulting in an integrated solids sample over the duration of a wet season. This confirmation is noteworthy because it is currently unclear whether the standard inline sediment trap integrates captured solids from all storm events throughout a deployment period, or whether the solids captured by the standard trap represent only a portion of the total solids fraction from a couple of storm events, such as the largest 10 percent of the storms during an entire storm season.

The conventional, or standard, trap's inherent limitations include a large profile, its inability to be effectively installed or capture adequate stormwater solids in small-pipe diameters, and the long processing and filtration times that are required at the end of a deployment period prior to solids analysis.

The present invention, in contrast, provides flexibility: it can be installed in different small-pipe diameters. Further, along with the prototype's ability to be easily installed and removed and the reduction in processing times as witnessed during this study, the present invention represents clear advantages over the standard sediment trap. Additionally, based on the results of this pilot study the SIFT also appears to capture a portion of the solids fraction during discrete storm events, resulting in a truly integrated solids sample over time, in contrast to the standard sediment trap.

DRAWING

FIG. 1 illustrates a common prior art trap in a common environment of use inside a stormwater pipeline.

FIG. 2 is a detailed front view of the prior-art sediment trap of FIG. 1.

FIG. 3 is a front view of a preferred embodiment of an inline sediment trap according the present invention shown in a typical environment of use.

FIG. 4 is a front view of an inline sediment trap according to one preferred embodiment of the present invention.

FIG. 6 is a right side view of the embodiment of FIG. 4.

FIG. 7 is a cut-away side view along the line 7-7 of FIG. 4.

FIG. 9 is an exploded assembly view showing various components of an inline sediment trap according to a preferred embodiment of the present invention.

FIG. 10 is an offset back view of the inline sediment trap of FIG. 9.

DESCRIPTION OF THE INVENTION

Figure 5:
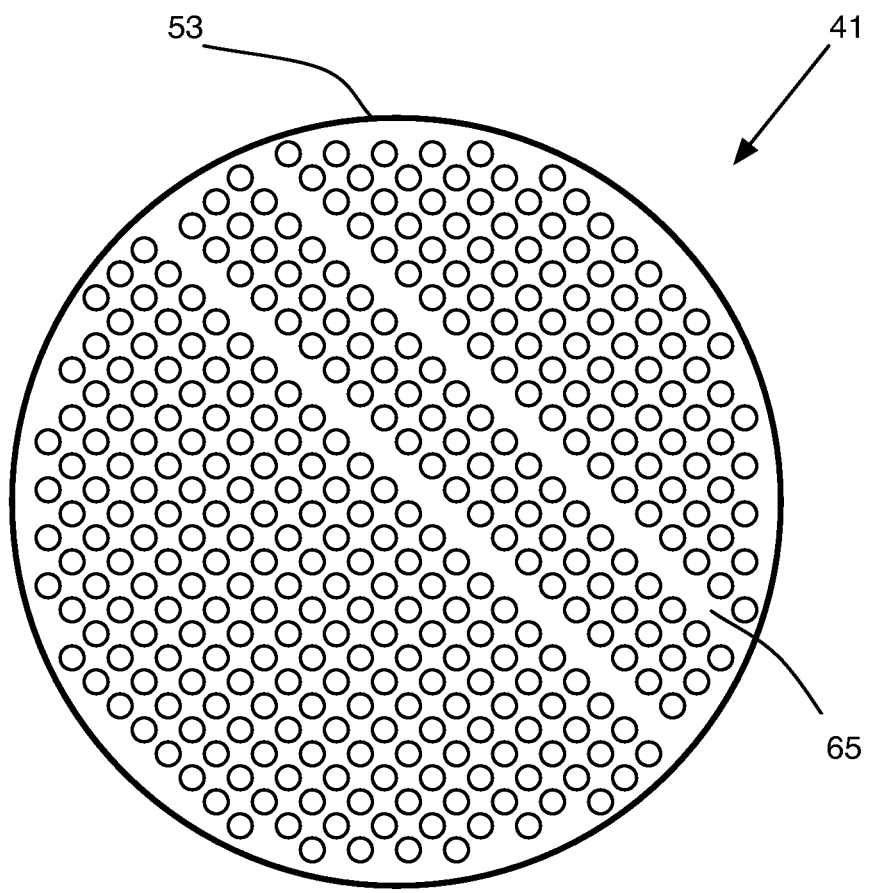
FIG. 5 is a back view of the embodiment of FIG. 4 with some elements omitted.

Possible preferred embodiments will now be described with reference to the drawings and those skilled in the art will understand that alternative configurations and combinations of components may be substituted without subtracting from the invention. Also, in some figures certain components are omitted to more clearly illustrate the invention.

FIG. 1 illustrates a known sediment trap 2 for placement in a pipe 1. This known trap 2 includes a housing 6 having one interior chamber, the housing 6 is supported by a bracket assembly 4. The bracket assembly is bolted to a sidewall of the pipe. The housing 6 is adapted to receive a plastic collection bottle 8 in the housing's one interior chamber and the bottle 8 is retained in the chamber by a securing band 12. The opening of the bottle is placed perpendicular to the flow of the effluent stream in the pipe. And sediment is deposited in the narrow opening, along with fluid and fluid with suspended solids. Because the bottle opening must be perpendicular to the flow of the effluent stream, this conventional trap requires a considerable amount of headroom, effectively limiting it to 30-inch diameter pipes or larger. Further, the band must be bolted to the sidewall of the pipe, limiting the possibility of subsequent adjustments to the trap's position and further preventing its application in smaller pipes that cannot accommodate a drill. Additionally, the collection bottle 8 consists of a single interior chamber with no internal partitions. This bottle is well-understood in the art.

FIG. 2 details this known sediment trap. A bolt-plate 22 couples to the pipe wall by means of a fastener 24. The plate carries one or more fins 26. Each fin has one or more through holes 30 for receiving another fastener 14. And the fins 26 couple by fasters to additional links 28 and supports 18, which couple to the cylindrical housing 6, which is sized to hold an industry-standard plastic bottle, which in this case is a Nalgene® model 2002-0032 narrow mouth, all-purpose Boston round HDPE 1-L plastic bottle with polypropylene screw closure purchased through Nurnberg Scientific of Portland, Oreg. Its dimensions are: height with closure, 216 mm; outside diameter, 91 mm; inside diameter of neck, 27 mm. The support, such as horizontal support 18 and vertical support 16 are welded to the housing. The vertical support 16 also carries the securing band, which retains the bottle in the housing by being circularly sized to be smaller than the bottle-body diameter, but larger than the open top of the bottle. Hand tools are required to secure the band 12 to the support after the bottle is in place, and are required again to remove the bottle when full of a collection sample. A common material for this trap is stainless steel due to the harsh environment of use and is relatively inert to reduce cross contamination of the sample media.

In contrast, the present invention in its various contemplated embodiments includes an in-line sediment trap 41 that is adapted to arrange in parallel to the effluent flow inside a pipe. FIG. 3 illustrates a pipe 1 with an in-line sediment trap 41 consisting of a trap assembly 51 coupled to an adjustable band assembly 43. When viewed from the front, as FIG. 3 shows, the effluent stream would flow into the page in along an imaginary path that would be orthogonal to the sheet of paper of FIG. 3. Visible from the front is the in-line sediment trap assembly 51 consisting of a housing body 53 with a partial front wall (weir) 57, and first or intermediate screen member 59 and three link arms 55 that couple the housing body to the adjustable band assembly 43. The adjustable band assembly 43 includes an adjuster mechanism 45 to alter the effective diameter of the band assembly so it can be tightened or loosened to install or remove against the interior wall of the pipe in a friction fit, without requiring one or more fasteners to pierce the sidewall or penetrate the pipe. As illustrated in FIG. 3, the adjuster band is in a loosened position, as would be used prior to installation or to remove the in-line trap, as would be appreciated by those skilled in this art.

FIG. 4, a front view of the trap assembly 51 according to a preferred embodiment of the present invention, shows a cylindrical housing body 53 having a partial front wall 57, which is approximately about ½-diameter of the opening. The housing body has a sidewall thickness of about ⅛ of an inch. Extending downward from the housing body, at least one, and preferably three linking members are coupled or welded or joined to an exterior portion of the housing and are adapted to support the housing to the adjuster band assembly (not shown in FIG. 4). The support links include a left link 63, a center support link 61, and a right link 55.

FIG. 5, a back view of the trap assembly 51 of FIG. 4, highlights the second or rear screen 65 disposed on the housing body 53. And, FIGS. 6 and 7 show a side view and cutaway view (along the line 7-7 of FIG. 4), respectively of this same embodiment of an inline sediment trap assembly 51. The first or intermediate screen 59 (as better viewed from the front view of FIG. 4, for example) has a first mesh size of 18-gauge (1270 micrometers (μm)) stamped stainless steel, and the rear or second screen 65 (as the rear view of FIG. 5 shows) has a smaller, second mesh size of approximately 228 μm. This enables collection of particulate matter of a predetermined size, as may be required for a particular study or environmental analysis. In other preferred embodiments the mesh sizes may be altered to affect different results as designed by the collection strategy desired.

Making general reference to FIGS. 3-7, a first preferred embodiment of the present invention includes an in-line sediment trap 41 including a trap assembly 51 coupled to an adjustable band assembly 43. The trap assembly 51 comprises a housing body 53 defining two chambers (see, specifically the cut-away view of FIG. 7, for example): A front half chamber 67 having at least one front-portion sidewall 68 and a partial front wall 57 disposed orthogonal to the at least one front-portion sidewall, and; A rear half chamber 73 having at least one rear-portion sidewall 70. The two chambers 67, 73 selectively couple by at least one, and preferably three locking members 69 consisting of a plate portion welded or otherwise attached to an exterior portion of one chamber, the plate extending to overlap a portion of the other chamber and having a through hole adapted to receive a threaded fastener 71 to attach to portion of the outer wall of the other chamber. Thus, as depicted in the preferred embodiment of FIGS. 6 and 7, the locking member 69 couples to the rear-chamber 73 and the removable fastener 71 selectively couples to the front chamber 67.

The housing further supports three links, one, the center link 61 is positioned under the front chamber, extending downward and having a plurality of holes for receiving fasteners provided by the adjuster band assembly (not shown in this figure). The other two links, a left link 63 and right link 55 extend downward from the rear-chamber 73 portion of the housing 53 and also have at least one through hole for receiving fastener or other linking members as required by the particular installation. Each linking member is welded to the housing 51.

The intermediate, or first, mesh screen 59 couples, either releasably or is welded to, the portion of the housing defining the front chamber 67, which thusly forms a rear wall of the front chamber 67. The second or rear mesh screen 65 is either releasably or welded to, the portion of the housing defining the rear chamber 73. In this manner the two chambers can be used to collect different sized particulates, and the housing can be disassembled to provide access to the second or rear chamber.

Figure 8:
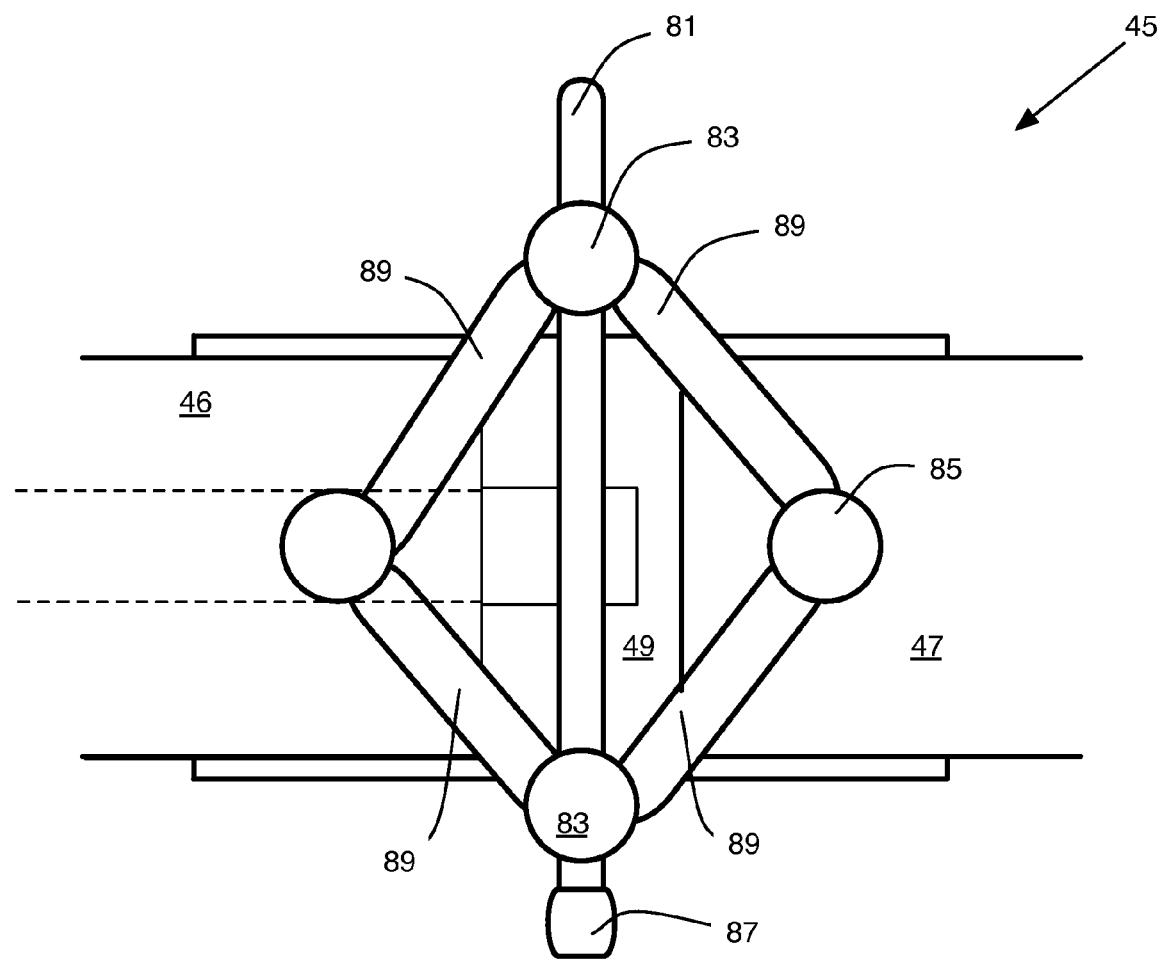
FIG. 8 is a detailed component view of a portion of the sediment trap of FIG. 3.

The present invention's sediment trap 41 includes an adjuster band assembly 43, which is well understood in this art. As such, the adjuster band varies in length depending on the pipe diameter and consists of a sheet of stainless steel with a width of 76 mm and thickness of 1 mm. The two opposite ends meet in proximity of each other and the effective diameter of the band is adjusted by a mechanical assembly 45. FIG. 8 details one such mechanical adjuster 45 for a typical band left end 46 and right end 47. A stainless steel threaded rod 81 having a hex-head rotating element 87 fixably coupled to one end enables a hand tool to cause the rod to rotate in two directions—one to release the band, the opposite to tighten the band. The threaded rod is 10 inches in length, ⅜ of an inch in diameter, and has a 9/16 of an inch hex-head.

Figure 11:
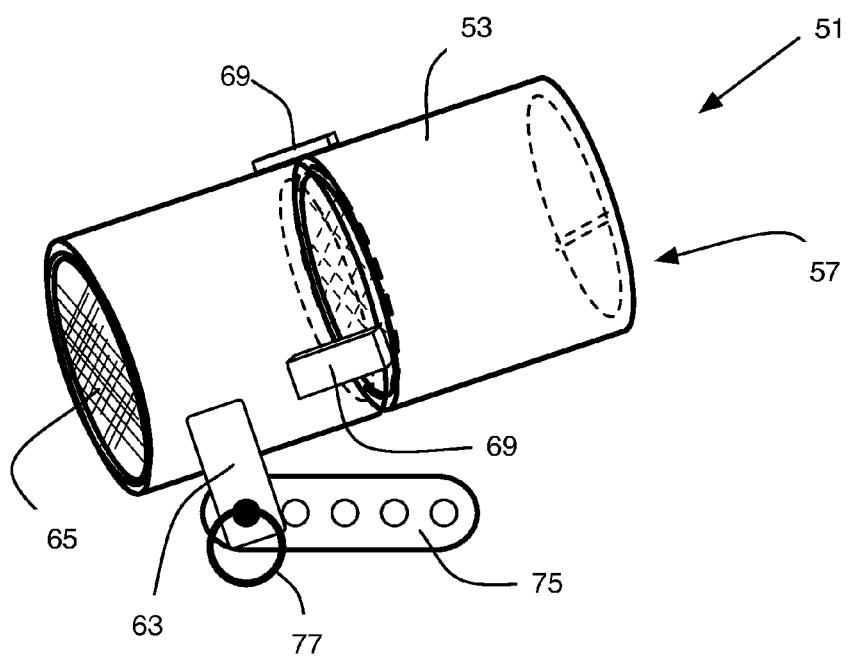
FIG. 11 is an offset back view of the sediment trap of FIG. 9 with additional components illustrated.

Making general reference to FIGS. 9, 10, and 11, another preferred embodiment of the present invention includes a sediment trap 41 for inline placement inside a pipeline. The sediment trap comprises a trap assembly 51 consisting of a housing body 53 defining two chambers, the body comprising a front housing body 67 (defining the first chamber) coupled (by means of at least one lock assembly 69) to a rear housing body 73 (defining the second chamber) and an intermediate screen member 59 disposed between the front housing and the rear housing.

The trap assembly has a first chamber defined by the front housing 67 further comprising at least one front-housing side wall 68 coupled to a partial front wall 57 wherein the partial front wall arranges on an end oppositely disposed from an end adjacent to the intermediate screen member 59.

The trap assembly has a second chamber defined by the rear housing 73, which includes at least one rear-housing sidewall 70 coupling to a rear screen mesh wall 65.

The housing body further comprises at least one linking member, or preferably three linking members (right link 55, center link 61, left link 63) adapted to enable the housing body to be coupled to an adjuster band assembly 43 wherein the housing body arranges inline with an effluent flow from the pipeline whereby the partial front wall arranges generally perpendicular to the effluent flow enabling the effluent flow to flow first into the intermediate screen and exit from the rear screen.

The preferred embodiments of the present invention contemplate the use of stainless steel, and illustrate the housing body as being cylindrical. However, other materials and shapes are also contemplated. For example, a rectilinear housing body may have a lower sidewall height to enable the invention to fit in smaller diameter pipes, or may have other configurations that are easier to manufacture. Other materials, including plastics and composites are also contemplated.

Additionally, a lipid bag or other semi-permeable membrane device can be attached to or inserted in the housing body to further or alternatively filter additional samples from the effluent stream. This modification would be well understood by those having ordinary skill in this art.

Although the invention has been particularly shown and described with reference to certain embodiments, it will be understood by those skilled in the art that various changes in form and detail may be made without departing from the spirit and scope of the invention.

We claim:

1. A sediment trap for inline placement inside a pipeline, the sediment trap comprising:
    a housing body defining two chambers, the housing body comprising a front half chamber coupled by means of at least one lock assembly to a rear half chamber and an intermediate screen member disposed between the front half chamber and the rear half chamber;

the front half chamber further comprising at least one front-portion sidewall coupled to a partial front wall, the partial front wall being disposed orthogonal to the at least on front-portion sidewall wherein the partial front wall arranges on an end oppositely disposed from the intermediate screen member;

the rear half chamber further comprising at least one rear-portion sidewall coupling to a rear screen;

the housing body further comprising at least one linking member adapted to enable the housing body to be coupled to an adjuster band assembly wherein the housing body arranges inline with an effluent flow from the pipeline whereby the partial front wall arranges generally perpendicular to the effluent flow enabling the effluent flow to flow first into the intermediate screen member and exit from the rear screen.

2. The sediment trap of claim 1, wherein the intermediate screen member is coupled to the at least one rear-portion sidewall.

3. The sediment trap of claim 1, wherein the front-portion sidewall is a first cylindrical body, the intermediate screen member including either a 18-gauge or 11270 μm stainless steel mesh, the rear-portion sidewall being a second cylindrical body, the rear screen including 228 μm stainless steel mesh backed by either 118-gauge or 1270 μm stainless steel mesh.

4. The sediment trap of claim 1, wherein the intermediate screen member comprises a mesh having a larger mesh opening size than the rear screen.

5. The sediment trap of claim 1, wherein the at least one linking member includes a right linking member coupled to at least one of the front-portion sidewall and the rear portion sidewall, a left linking member coupled to at least one of the front-portion sidewall and the rear portion sidewall, and a center linking member coupled to at least one of the front-portion sidewall and the rear portion sidewall.

6. The sediment trap of claim 5, wherein the adjuster band is coupled to at least one of the right, left, and center linking members.

7. The sediment trap of claim 6, further comprising a mechanism for adjusting an effective diameter of the adjuster band relative to an interior sidewall of the pipeline, the mechanism comprising a threaded rod that is selectively rotatable causing a plurality of interconnected scissor-type linking arms to expand or contract the effective diameter of the adjuster band dependent on whether the threaded rod is rotated clockwise or anti-clockwise.

8. The sediment trap of claim 1, wherein the at least one linking member includes a center linking member coupled to a front portion of the housing body, and right and left linking members coupled to a rear portion of the housing body.

9. A method for collecting suspended sediment in a pipeline comprising:
providing a sediment trap comprising
a housing body defining two chambers, the housing body comprising a front housing body coupled by at least one lock assembly to a rear housing body, and an intermediate screen member disposed between the front housing body and the rear housing body;
a first chamber defined by the front housing body further comprising at least one front-housing sidewall coupled to a partial front wall wherein the partial front wall arranges on an end oppositely disposed from an end adjacent to the intermediate screen member;
the rear housing body further comprising at least one rear-housing sidewall coupling to a rear wall comprising a screen mesh wall;
the housing body further comprising at least one linking member adapted to enable the housing body to be coupled to an adjuster band assembly wherein the housing body arranges inline with an effluent flow from the pipeline whereby the partial front wall arranges generally perpendicular to the effluent flow enabling the effluent flow to flow first into the intermediate screen member and exit from the screen mesh wall;
installing the sediment trap in the pipeline; and
using the sediment trap to collect a sample of solids.

10. A method for collecting suspended sediment in a pipeline comprising:
providing a sediment trap comprising
a housing body defining two chambers, the housing body comprising a front half chamber coupled by at least one lock assembly to a rear half chamber, and an intermediate screen member disposed between the front half chamber and the rear half chamber,
the front half chamber further comprising at least one front-portion sidewall coupled to a partial front wall, the partial front wall being disposed orthogonal to the at least one front-portion sidewall wherein the partial front wall arranges on an end of the front half chamber oppositely disposed from the intermediate screen member,
the rear half chamber further comprising at least on rear-portion sidewall coupling to a rear screen,
the housing body further comprising at least one linking member adapted to enable the housing body to be coupled to an adjuster band assembly wherein the housing body arranges inline with an effluent flow from the pipeline whereby the partial front wall arranges generally perpendicular to the effluent flow enabling the effluent flow to flow first into the intermediate screen member and exit from the rear screen;
installing the sediment trap in the pipeline using the adjuster band assembly; and
collecting a sample of solids.

* * * * *